(12) United States Patent
Ini et al.

(10) Patent No.: US 7,759,500 B2
(45) Date of Patent: Jul. 20, 2010

(54) 2-(N-METHYL-PROPANAMINE)-3-(2-NAPHTHOL)THIOPHENE, AN IMPURITY OF DULOXETINE HYDROCHLORIDE

(75) Inventors: Santiago Ini, Haifa (IL); Alexei Ploutno, Bat-Yam (IL); Anita Liberman, Tel-Aviv (IL); Mili Abramov, Givataim (IL); Osnat Porter-Kleks, Petach-Tikva (IL); Dina Berezovsky, Petach-Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 716 days.

(21) Appl. No.: 11/634,693

(22) Filed: Dec. 5, 2006

(65) Prior Publication Data

US 2007/0191472 A1 Aug. 16, 2007

Related U.S. Application Data

(60) Provisional application No. 60/742,621, filed on Dec. 5, 2005.

(51) Int. Cl.
*C07D 333/12* (2006.01)
(52) U.S. Cl. ........................................ 549/74
(58) Field of Classification Search ................ 549/74
See application file for complete search history.

(56) References Cited

U.S. PATENT DOCUMENTS

| | | | |
|---|---|---|---|
| 3,433,804 | A | 3/1969 | Hollinger et al. |
| 4,956,388 | A | 9/1990 | Robertson et al. |
| 5,023,269 | A | 6/1991 | Robertson et al. |
| 5,362,886 | A | 11/1994 | Berglund |
| 5,371,240 | A | 12/1994 | Slemon |
| 5,491,243 | A | 2/1996 | Berglund |
| 5,508,276 | A | 4/1996 | Anderson et al. |
| 5,910,319 | A | 6/1999 | Anderson et al. |
| 6,333,198 | B1 | 12/2001 | Edmeades et al. |
| 6,541,668 | B1 | 4/2003 | Kjell et al. |
| 2004/0249170 | A1 | 12/2004 | Borghese |
| 2005/0197503 | A1 | 9/2005 | Schiffers et al. |
| 2006/0063943 | A1 | 3/2006 | Sakai et al. |
| 2006/0165776 | A1 | 7/2006 | Sesha |
| 2006/0194869 | A1 | 8/2006 | Ini et al. |
| 2006/0205956 | A1 | 9/2006 | Ramachandra et al. |
| 2006/0276660 | A1 | 12/2006 | Ini et al. |
| 2007/0167636 | A1 | 7/2007 | Butchko et al. |

FOREIGN PATENT DOCUMENTS

| | | |
|---|---|---|
| EP | 0 273 658 | 7/1988 |
| EP | 0 457 559 | 11/1991 |
| EP | 0 654 264 | 5/1995 |
| EP | 1 820 800 A1 | 8/2007 |
| JP | 2004 123596 | 4/2004 |
| WO | WO 2004/056795 | 7/2004 |
| WO | WO 2005/019199 | 3/2005 |
| WO | WO 2005/108386 | 11/2005 |
| WO | WO 2006/027798 | 3/2006 |
| WO | WO 2006/045255 | 5/2006 |
| WO | WO 2006/081515 | 8/2006 |
| WO | WO 2006/096809 | 9/2006 |
| WO | WO 2006/099433 | 9/2006 |
| WO | WO 2006/099468 A2 | 9/2006 |
| WO | WO 2006/126213 | 11/2006 |
| WO | WO 2007/034503 A | 3/2007 |
| WO | WO 2007/067581 A1 | 6/2007 |
| WO | WO 2007/096707 | 8/2007 |

OTHER PUBLICATIONS

Olsen, B.A. et al., "HPLC Method Development for Duloxetine Hydrochloride Using a Combination of Computer-Based Solvent Strength Optimization and Solvent Selectivity Mixture Design," J. Liq. Chrom. & Rel. Technol, 1996 19(12)1993.
Kamal, et al., "Chemoenzymatic Synthesis of Duloxetine And Its Enantiomer: Lipase-Catalyzed Resolution Of 3-Hydroxy-3-(2-Thienyl) Propanenitrile", *Tetrahedron Letters*, 2003, pp. 4783-4787, vol. 44, No. 25.
Astleford, B.A & Weigel, L.O., "Resolution Versus Stereoselective Synthesis in Drug Development: Some Case Studies," in Chirality in Industry II: Developments in the Commercial Manufacture and Applications of Optically Active Compounds, 99-117 (John Wiley & Sons, 1997).
Bopp, R.J. et al., "Practical Considerations for Chiral Separations of Pharmaceutical Compounds," *LG-GC*, 6(6): 514, 516, 518, 520, 522 (Advanstar Comm., Cleveland OH 1988).
Fujima, Yoshito et al., "Synthesis of (S)-3-(N-Methylamino)-1-(2-thienyl)propan-1-ol: Revisiting Eli Lilly's Resolution-Racemization-Recycle Synthesis of Duloxetine for Its Robust Processes," *Organic Process Research & Development*, 10(5): 905-913 (2006).
Sakai, K. et al., "Resolution of 3-(methylamino)-1-(2-thienyl)propan-1-ol, a new key intermediate for duloxetine, with (S)-mandelic acid," *Tetrahedron: Asymmetry*, 14(12): 1631-1636 (2003).
CRC Handbook of Optical Resolutions Via Diastereomeric Salt Formation CRC: Boca Raton, 2002, pp. 93-95, 504-518.
L.A. Sorbera, et al., "Duloxetine Oxalate", *Drugs of the Future*, vol. 25, No. 9, pp. 907-916, (2000).
Valenta, V. et al., "Potential Antidepressants: 3-aryl-3-(arylthio)propylamines as selective inhibitors of 5-hydroxytryptamine reuptake in the brain", *Collection of Czechoslovak Chemical Communications*, 56(7): 1525-1533 (1991).
Corey et al., "Reduction of Carbonyl Compounds with Chiral Oxazaborolidine Catalysts: A New Paradigm for Enantioselective Catalysis and a Powerful New Synthetic Method," Angew. Chem. Int. Ed. (1998) vol. 37(15) p. 1986.
March, J., Advanced Organic Chemistry (4th ed., 1992, Wiley).
ICH Good Manufacturing Practice Guide for Active Pharmaceutical Ingredients, Q7A, Current Step 4 Version, Nov. 10, 2000.
Snyder, L.R. et al., Introduction to Modern Liquid Chromatography, 549, 552, 571, 572 (2d ed., 1979, Wiley & Sons, New York).

(Continued)

*Primary Examiner*—Taofiq A Solola
(74) *Attorney, Agent, or Firm*—Kenyon & Kenyon LLP

(57) ABSTRACT

The invention encompasses 2-(N-methyl-propanamine)-3-(2-naphthol)thiophene, a duloxetine hydrochloride impurity, as well as its use as a reference marker and reference standard.

25 Claims, No Drawings

OTHER PUBLICATIONS

Strobel, H.A. et al., Chemical Instrumentation: A Systematic Approach, 391-393, 894, 921,-922, 924-925, 935, 953 (3d ed., 1989, Wiley & Sons, New York).

Wheeler W. J., et al., "An Asymmetric Synthesis of Duloxetine Hydrochloride, a Mixed Uptake Inhibitor of Serotonin and Norepinephrine, and its C-14 Labeled Isotopomers", *J. Label .Cpds. Radiopharm*, 36(3): 213-223 (1995).

2-(N-METHYL-PROPANAMINE)-3-(2-NAPHTHOL)THIOPHENE, AN IMPURITY OF DULOXETINE HYDROCHLORIDE

CROSS-REFERENCE TO RELATED APPLICATIONS

This application claims the benefit of priority to U.S. provisional application Ser. No. 60/742,621, filed Dec. 5, 2005, hereby incorporated by reference.

FIELD OF THE INVENTION

The invention encompasses isolated 2-(N-methyl-propanamine)-3-(2-naphthol)thiophene, a duloxetine hydrochloride impurity, as well as its use as a reference marker and reference standard.

BACKGROUND OF THE INVENTION

Duloxetine hydrochloride, (S)-(+)-N-methyl-3-(1-naphthalenyloxy)-3-(2-thienyl)propanamine hydrochloric acid salt, is a dual reuptake inhibitor of the neurotransmitters serotonin and norepinephrine. Duloxetine hydrochloride is used for the treatment of stress urinary incontinence ("SUI"), depression, and pain management and is commercially available as CYMBALTA®. Duloxetine hydrochloride has the following chemical structure:

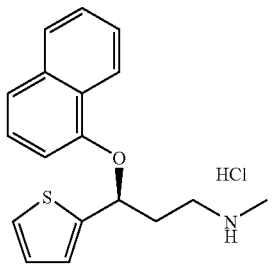

U.S. Pat. No. 5,023,269 ("'269 patent") discloses a class of 3-aryloxy-3-substituted propanamines, including duloxetine, as well as pharmaceutically acceptable acid addition salts thereof. See '269 patent, col. 1, 11. 27-58. The '269 patent also discloses a general process for preparing compounds of the class, and exemplifies, inter alia, the preparation of duloxetine oxalate. See '269 patent, col. 7, 11. 5-30 (example 2). In the '269 patent, duloxetine is prepared by reacting N,N-dimethyl-3-(2-thienyl)-3-hydroxypropanamine with fluoronaphthalene, followed by demethylation with phenyl chloroformate or trichloroethyl chloroformate and basic hydrolysis. See '269 patent, col. 6, 1. 13 to col. 7, 1. 30 (examples 1 and 2).

European patent No. 457559 and U.S. Pat. Nos. 5,491,243 ("'243 patent") and 6,541,668 provide synthetic routes for the preparation of duloxetine. The conversion of duloxetine to its hydrochloride salt is disclosed in the '243 patent, as well as in Wheeler W. J., et al., *J. Label. Cpds. Radiopharm.*, 1995, 36, 312. In both the '243 patent and the Wheeler article, the conversion of duloxetine to its hydrochloride salt is performed in ethyl acetate under specified conditions.

Like any synthetic compound, duloxetine hydrochloride can contain extraneous compounds or impurities. These impurities may be, for example, starting materials, by-products of the reaction, products of side reactions, or degradation products. Impurities in duloxetine hydrochloride, or any active pharmaceutical ingredient ("API"), are undesirable and, in extreme cases, might even be harmful to a patient being treated with a dosage form containing the API.

The purity of an API produced in a manufacturing process is critical for commercialization. The U.S. Food and Drug Administration ("FDA") requires that process impurities be maintained below set limits. For example, in its ICH Q7A guidance for API manufacturers, the FDA specifies the quality of raw materials that may be used, as well as acceptable process conditions, such as temperature, pressure, time, and stoichiometric ratios, including purification steps, such as crystallization, distillation, and liquid-liquid extraction. See ICH Good Manufacturing Practice Guide for Active Pharmaceutical Ingredients, Q7A, Current Step 4 Version (Nov. 10, 2000).

The product of a chemical reaction is rarely a single compound with sufficient purity to comply with pharmaceutical standards. Side products and by-products of the reaction and adjunct reagents used in the reaction will, in most cases, also be present in the product. At certain stages during processing of an API, such as duloxetine hydrochloride, it must be analyzed for purity, typically, by high performance liquid chromatography ("HPLC") or thin-layer chromatography ("TLC"), to determine if it is suitable for continued processing and, ultimately, for use in a pharmaceutical product. The FDA requires that an API is as free of impurities as possible, so that it is as safe as possible for clinical use. For example, the FDA recommends that the amounts of some impurities be limited to less than 0.1 percent. See ICH Good Manufacturing Practice Guide for Active Pharmaceutical Ingredients, Q7A, Current Step 4 Version (Nov. 10, 2000).

Generally, side products, by-products, and adjunct reagents (collectively "impurities") are identified spectroscopically and/or with another physical method, and then associated with a peak position, such as that in a chromatogram, or a spot on a TLC plate. See Strobel, H. A., et al., CHEMICAL INSTRUMENTATION: A SYSTEMATIC APPROACH, 953, 3d ed. (Wiley & Sons, New York 1989). Once a particular impurity has been associated with a peak position, the impurity can be identified in a sample by its relative position in the chromatogram, where the position in the chromatogram is measured in minutes between injection of the sample on the column and elution of the impurity through the detector. The relative position in the chromatogram is known as the "retention time."

The retention time can vary about a mean value based upon the condition of the instrumentation, as well as many other factors. To mitigate the effects such variations have upon accurate identification of an impurity, practitioners often use "relative retention time" ("RRT") to identify impurities. See supra Strobel at 922. The RRT of an impurity is calculated by dividing the retention time of the impurity by the retention time of a reference marker. The reference marker may be the API in which the impurity is present, or may be another compound that is either present in or added to the sample. A reference marker should be present in the sample in an amount that is sufficiently large to be detectable, but not in an amount large enough to saturate the column.

Those skilled in the art of drug manufacturing research and development understand that a relatively pure compound can be used as a "reference standard." A reference standard is similar to a reference marker, except that it may be used not only to identify the impurity, but also to quantify the amount of the impurity present in the sample.

A reference standard is an "external standard," when a solution of a known concentration of the reference standard and an unknown mixture are analyzed separately using the same technique. See supra Strobel at 924; Snyder, L. R., et al., INTRODUCTION TO MODERN LIQUID CHROMATOGRAPHY, 549, 2d ed. (John Wiley & Sons, New York 1979). The amount of the impurity in the sample can be determined by comparing the magnitude of the detector response for the reference standard to that for the impurity. See U.S. Pat. No. 6,333,198, hereby incorporated by reference.

The reference standard can also be used as an "internal standard," i.e., one that is directly added to the sample in a predetermined amount. When the reference standard is an internal standard, a "response factor," which compensates for differences in the sensitivity of the detector to the impurity and the reference standard, is used to quantify the amount of the impurity in the sample. See supra Strobel at 894. For this purpose, the reference standard is added directly to the mixture, and is known as an "internal standard." See supra Strobel at 925; Snyder at 552.

The technique of "standard addition" can also be used to quantify the amount of the impurity. This technique is used where the sample contains an unknown detectable amount of the reference standard. In a "standard addition," at least two samples are prepared by adding known and differing amounts of the internal standard. See supra Strobel at 391-393; Snyder at 571-572. The proportion of the detector response due to the reference standard present in the sample can be determined by plotting the detector response against the amount of the reference standard added to each of the samples, and extrapolating the plot to zero. See supra Strobel at 392, FIG. 11.4.

Duloxetine hydrochloride may contain the impurity 2-(N-methyl-propanamine)-3-(2-naphthol)thiophene. There is, therefore, a need in the art to detect, isolate, and remove the 2-(N-methyl-propanamine)-3-(2-naphthol)thiophene impurity from samples of duloxetine hydrochloride.

SUMMARY OF THE INVENTION

In one embodiment, the invention encompasses isolated 2-(N-methyl-propanamine)-3-(2-naphthol)thiophene.

In another embodiment, the invention encompasses a process for preparing 2-(N-methyl-propanamine)-3-(2-naphthol)thiophene comprising: heating a mixture of duloxetine and at least one solvent, wherein the solvent is a $C_2$-$C_8$ ether, a $C_5$-$C_8$ aliphatic or $C_6$-$C_{12}$ aromatic hydrocarbon, a $C_1$-$C_8$ alcohol, dimethyl sulfoxide (DMSO), dimethylacetamide (DMA), dimethylformamide (DMF), 1-methyl-2-pyrrolidinone (NMP), acetonitrile or propylene glycol methyl ether (PGME); and maintaining the mixture for a period of time sufficient to obtain 2-(N-methyl-propanamine)-3-(2-naphthol)thiophene.

In another embodiment, the invention encompasses a process for preparing duloxetine hydrochloride having less than about 0.08% area by HPLC of 2-(N-methyl-propanamine)-3-(2-naphthol)thiophene comprising: providing a mixture of duloxetine hydrochloride having more than about 0.08% area by HPLC of 2-(N-methyl-propanamine)-3-(2-naphthol)thiophene in at least one polar solvent, wherein the polar solvent is a $C_{2-5}$ ketone, $C_{2-5}$ alkyl ester, $C_{2-8}$ alkyl ether or $C_{2-8}$ alkanol; maintaining the mixture for a period of time sufficient to obtain duloxetine hydrochloride having less than about less than about 0.08% area by HPLC of 2-(N-methyl-propanamine)-3-(2-naphthol)thiophene. Preferably the duloxetine hydrochloride has less than about 0.06% area by HPLC of 2-(N-methyl-propanamine)-3-(2-naphthol)thiophene, more preferably the duloxetine hydrochloride has less than about 0.02% area by HPLC of 2-(N-methyl-propanamine)-3-(2-naphthol)thiophene, and most preferably is substantially free of 2-(N-methyl-propanamine)-3-(2-naphthol)thiophene, i.e., the amount of 2-(N-methyl-propanamine)-3-(2-naphthol)thiophene is below that which can be detected by HPLC.

The invention also encompasses the use of 2-(N-methyl-propanamine)-3-(2-naphthol)thiophene as a reference marker to analyze the purity of duloxetine HCl.

The invention also encompasses the use of 2-(N-methyl-propanamine)-3-(2-naphthol)thiophene as a reference standard to quantify the amount of a 2-(N-methyl-propanamine)-3-(2-naphthol)thiophene impurity in a sample of duloxetine HCl.

The invention also encompasses a quantification method of 2-(N-methyl-propanamine)-3-(2-naphthol)thiophene in a duloxetine sample.

In a further embodiment, the invention encompasses an analytical method for testing the impurity profile of duloxetine HCl. The method is also suitable for analyzing and assaying duloxetine HCl and 2-(N-methyl-propanamine)-3-(2-naphthol)thiophene.

DETAILED DESCRIPTION OF THE INVENTION

The invention provides methods for detecting and isolating the duloxetine hydrochloride impurity 2-(N-methyl-propanamine)-3-(2-naphthol)thiophene, as well as methods for removing the impurity from samples of duloxetine hydrochloride.

As used herein, the term "reference standard" refers to a compound that may be used both for quantitative and qualitative analysis of an active pharmaceutical ingredient. For example, the HPLC retention time of the reference standard allows a relative retention time with respect to the active pharmaceutical ingredient to be determined, thus making qualitative analysis possible. Furthermore, the concentration of the compound in solution before injection into an HPLC column allows the areas under the HPLC peaks to be compared, thus making quantitative analysis possible.

A "reference marker" is used in qualitative analysis to identify components of a mixture based upon their position, e.g., in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

The invention encompasses isolated 2-(N-methyl-propanamine)-3-(2-naphthol)thiophene ("DLX—ISO—OH"), which is an impurity in duloxetine hydrochloride. DLX—ISO—OH is represented by the following chemical structure:

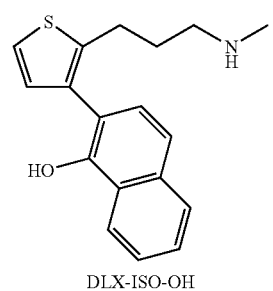

DLX-ISO-OH

DLX—ISO—OH is characterized by at least one of: $^1$H NMR (400 MHz, DMSO d$_6$) δ(ppm): 8.56 (m, 1H), 8.12 (m, 1H), 7.76 (m, 1H), 7.75 (m, 1H), 7.69 (d, J=5.1 Hz, 1H), 7.65 (d, J=8.3 Hz, 1H), 7.49 (d, J=8.3 Hz, 1H), 7.27 (d, J=5.1 Hz, 1H), 3.03 (t, J=7.4 Hz, 2H), 2.76 (t, J=6.5 Hz, 2H), 2.03 (m, 2H), 2.49 (s, 3H); $^{13}$C {$^1$H}NMR (100 MHz): δ 151.4, 141.7, 136.5, 134.7, 130.9, 129.9, 128.2, 127.1, 126.7, 125.6, 123.5, 122.9, 119.0, 118.9, 51.2, 36.5, 31.4, 26.8; and [FAB(+)] m/z 298 (M-K+H)$^+$, [CI] m/z 298 (M-K+H)$^+$.

Not to be limited by theory, it is believed that DLX—ISO—OH is produced during the basic hydrolysis step in the process for preparing duloxetine. The heating of the reaction mixture during the basic hydrolysis step may initiate a Claisen-type [3,3]-sigmatropic rearrangement of duloxetine, to form an intermediate which quickly tautomerizes to an ortho-substituted naphthol. The presence of base then promotes the elimination of the proton from the ortho-substituted napthol to regenerate the thiophene ring. This proposed mechanism is illustrated in Scheme 1.

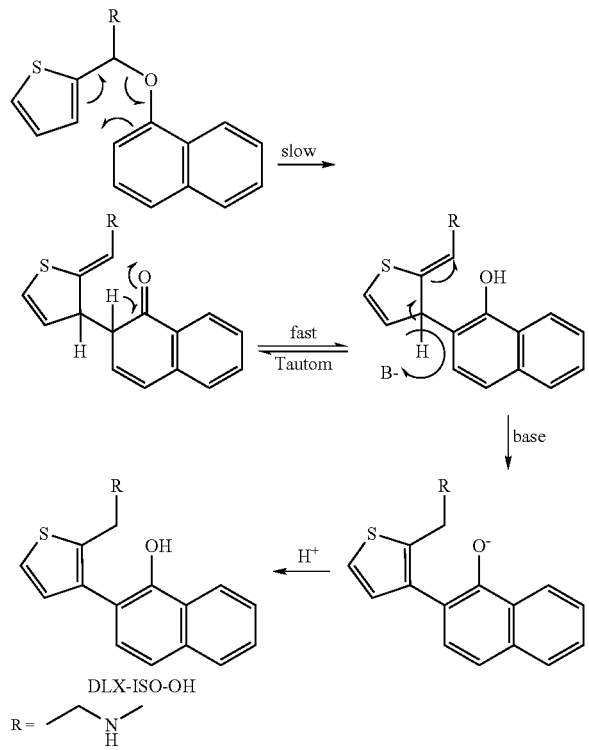

Scheme 1. Proposed mechanism for the formation of DLX-ISO-OH

The invention also encompasses a process for preparing DLX—ISO—OH comprising: heating a mixture of duloxetine and at least one solvent, wherein the solvent is a C$_2$-C$_8$ ether, a C$_5$-C$_8$ aliphatic or C$_6$-C$_{12}$ aromatic hydrocarbon, a C$_1$-C$_8$ alcohol, dimethyl sulfoxide, dimethylacetamide, dimethylformamide, 1-methyl-2-pyrrolidinone, acetonitrile or propylene glycol methyl ether; and maintaining the mixture for a period of time sufficient to obtain DLX—ISO—OH.

Preferably, the solvent is propylene glycol methyl ether (PGME) or toluene.

Preferably, at least one inorganic base is combined with the mixture in order to catalyze the production of DLX—ISO—OH. Preferably, the inorganic base is combined with the mixture in a catalytic amount. Typically, the inorganic base is an alkaline metal hydroxide or an alkaline earth metal hydroxide. Preferably, the inorganic base is potassium hydroxide, sodium hydroxide, lithium hydroxide, magnesium hydroxide, or calcium hydroxide. More preferably, the inorganic base is potassium hydroxide.

Typically, the mixture is heated at a temperature of about 60° C. to about reflux. Preferably, the mixture is heated at a temperature of about reflux.

Preferably, the mixture is maintained for at least about 96 hours to obtain DLX—ISO—OH. More preferably, the mixture is maintained for about 96 hours to about 120 hours.

The DLX—ISO—OH thus obtained may then be recovered by extraction. In one embodiment, the DLX—ISO—OH is recovered by adding a second solvent to the mixture to obtain a two-phase system having a water miscible phase and a water immiscible phase, wherein the second solvent is at least one of water, a C$_2$-C$_9$ ether, a C$_1$-C$_8$ alcohol, and a C$_5$-C$_8$ aliphatic or C$_6$-C$_{12}$ aromatic hydrocarbon, dimethyl sulfoxide, dimethylacetamide, dimethylformamide, 1-methyl-2-pyrrolidinone, acetonitrile or propylene glycol methyl ether; and recovering the DLX—ISO—OH from the water immiscible phase. Preferably, the second solvent is a mixture of water and toluene. Typically, the mixture is cooled to about room temperature before the addition of the second solvent.

The DLX—ISO—OH may be recovered by any method known to one of skill in the art. Suitable methods include, but are not limited to, filtering and washing the DLX—ISO—OH, followed by drying. Preferably, the DLX—ISO—OH is dried at about 50° C. for about 12 hours at a pressure below about 100 mmHg in a vacuum oven.

Optionally, the process may further comprise converting the DLX—ISO—OH to its hydrochloride salt, (DLX—ISO—OH)—HCl. Preferably, the DLX—ISO—OH is converted to (DLX—ISO—OH)—HCl by combining the mixture with HCl to obtain (DLX—ISO—OH)—HCl; and precipitating the (DLX—ISO—OH)—HCl from the mixture.

The invention also encompasses a process for preparing duloxetine hydrochloride having less than about 0.08% area by HPLC of DLX—ISO—OH comprising: providing a mixture of duloxetine hydrochloride having more than about 0.08% area by HPLC of DLX—ISO—OH in at least one polar solvent, wherein the polar solvent is a C$_{2-5}$ ketone, C$_{2-5}$ alkyl ester, C$_{2-8}$ alkyl ether or C$_{2-8}$ alkanol; and maintaining the mixture for a period of time sufficient to obtain duloxetine hydrochloride having less than about 0.08% area by HPLC of DLX—ISO—OH.

Preferably, the polar solvent is acetone, methyl ethyl ketone (MEK), ethyl acetate, methyl t-butyl ether (MTBE), ethanol, isopropanol, or n-butanol. More preferably, the polar solvent is acetone.

Typically, the mixture is maintained for at least about 1 hour to obtain a precipitate of duloxetine hydrochloride. Preferably, the mixture is maintained for about 1 hour to about 12 hours.

Preferably, the duloxetine hydrochloride thus obtained has less than about 0.06% area by HPLC of DLX—ISO—OH, more preferably the duloxetine HCl has less than about 0.02% area by HPLC of DLX—ISO—OH, and most preferably the duloxetine HCl is substantially free of DLX—ISO—OH.

The above-described process may be repeated in order to reduce the content of DLX—ISO—OH in the duloxetine hydrochloride even further.

The DLX—ISO—OH is useful as a reference marker for duloxetine hydrochloride. As such, it may be used in order to detect the presence of DLX—ISO—OH in a sample of duloxetine hydrochloride.

The invention encompasses the use of DLX—ISO—OH as a reference marker to analyze the purity of duloxetine HCl.

The method comprises: a) providing a reference sample comprising duloxetine hydrochloride and DLX—ISO—OH; b) analyzing the reference sample by HPLC and determining the relative retention time of DLX—ISO—OH compared to duloxetine hydrochloride; c) analyzing a sample of duloxetine hydrochloride by HPLC and determining the relative retention times of the contents of the sample as compared to duloxetine hydrochloride; and d) comparing the relative retention times calculated in step c) to the relative retention time calculated in step b) for DLX—ISO—OH, wherein if any of the relative retention times calculated in step c) are substantially the same as the relative retention time of DLX—ISO—OH, DLX—ISO—OH is present in the sample of duloxetine hydrochloride.

The DLX—ISO—OH is also useful as a reference standard for duloxetine hydrochloride. As such, it may be used in order to quantify the amount of DLX—ISO—OH in a sample of duloxetine hydrochloride.

The DLX—ISO—OH may be used as an external reference standard for duloxetine hydrochloride. The invention encompasses the use of DLX—ISO—OH as a reference standard for determining the amount of DLX—ISO—OH in a duloxetine hydrochloride sample comprising: a) measuring by HPLC the area under the peak corresponding to DLX—ISO—OH in a sample of duloxetine hydrochloride having an unknown amount of DLX—ISO—OH; b) measuring by HPLC the area under a peak corresponding to DLX—ISO—OH in a reference standard comprising a known amount of DLX—ISO—OH; and c) determining the amount of DLX—ISO—OH in the duloxetine hydrochloride sample by comparing the area calculated in step a) to the area calculated in step b).

The invention further encompasses a quantification method for determining the amount of DLX—ISO—OH in a duloxetine hydrochloride sample using DLX—ISO—OH. The method comprises: a) measuring by HPLC the area under the peak corresponding to DLX—ISO—OH in a sample of duloxetine hydrochloride having an unknown amount of DLX—ISO—OH; b) measuring by HPLC the area under a peak corresponding to duloxetine hydrochloride in a reference standard having a known amount of duloxetine hydrochloride; and c) determining the amount of DLX—ISO—OH in the duloxetine hydrochloride sample by comparing the area calculated in step a) to the area calculated in step b).

The invention further encompasses an analytical method for testing the impurity profile of duloxetine HCl.

In one embodiment, the HPLC analysis is performed with a high performance liquid chromatograph having a Hypersil Gold (150*4.6 5μ) column and an ultraviolet detector at 230 nm. According to the maker, a Hypersil Gold column is a C-18 column made up of end-capped, deactivated silica with a pore size of 175 Å and a particle size of 1.9, 3, 5, 8, or 12 μm. The sample to be analyzed is dissolved in a 1:1 (volume:volume) mixture of water and acetonitrile and gradient eluted through the column with a mixture of 0.02 M $KH_2PO_4$: methanol: tetrahydrofuran (63:28.8:8.2), followed by a mixture of 0.02 M $KH_2PO_4$: acetonitrile (20:80).

Having described the invention with reference to certain preferred embodiments, other embodiments will become apparent to one skilled in the art from consideration of the specification. The invention is further defined by reference to the following examples describing in detail the preparation and analysis of duloxetine hydrochloride. It will be apparent to those skilled in the art that many modifications, both to materials and methods, may be practiced without departing from the scope of the invention.

EXAMPLES

Nuclear Magnetic Resonance ("NMR") Spectroscopy

NMR spectroscopy was performed on a Bruker DPX (400MHz for $^1$H-NMR, 100 MHz for $^{13}$C-NMR) using DMSO-d6 solvent.

High Performance Liquid Chromatography ("HPLC")

A high performance liquid chromatograph with a Hypersil Gold (150*4.6 5μ) column and an ultraviolet detector at 230 nm was used. The flow rate was 1 ml/minute. The detection limit was 0.02%.

The mobile phase was comprised of two eluents (A and B). Eluent A was 63% (0.02M $KH_2PO_4$ at a pH of 2.5), 28.8% methanol, and 8.2% tetrahydrofuran. Eluent B was 20% (0.02M $KH_2PO_4$ at a pH of 2.5) and 80% acetonitrile.

Samples of duloxetine hydrochloride were dissolved in a 1:1 (volume:volume) mixture of water and acetonitrile. Each sample contained about 0.2 mg duloxetine hydrochloride per milliliter of solvent. The samples were carried through the column by gradient elution under the following conditions: 15 minutes of 100% eluent A, followed by an increase in eluent B from 0 to 75% from 15 to 60 minutes.

Example 1

Preparation of DLX—ISO—OH in PGME

A 100 ml three necked flask equipped with a mechanical stirrer, thermometer, and condenser was charged with a mixture of 4.2 g of duloxetine in 42 ml PGME and 5.2 g of KOH (85%). The mixture was then heated to reflux and stirred for 96 hours.

After cooling the mixture to room temperature, 50 ml of water and 50 ml of toluene were added, and the resulting organic phase was washed (4×50 ml) with water, cooled to 0° C. and stirred for an additional hour, during which time DLX—ISO—OH precipitated. The DLX—ISO—OH was filtered from the water immiscible phase, washed with 20 ml of toluene, and dried in a vacuum oven at 50° C. overnight.

Example 2

Preparation of (DLX—ISO—OH)—HCl in PGME

A 1 liter reactor equipped with a mechanical stirrer, thermometer, and condenser was charged with a mixture of 48.5 g of duloxetine in 240 ml PGME and 50.5 g of KOH (85%). The mixture was then heated to reflux and stirred for 144 hours. After cooling, the mixture was evaporated to dryness and 200 ml of water and 200 ml of dichloromethane were added. The resulting mixture was acidified to pH 12 and stirred overnight, during which time a solid precipitated.

The precipitated solid was filtered, added to a mixture of 80 ml dichloromethane and 80 ml water, and acidified to pH=2-3 (HCl [5%]). The organic phase was separated from the mixture and the water was extracted with dichloromethane. Both of the organic phases were combined, dried over sodium sulfate and evaporated to dryness to give 18 g (34% yield) of (DLX—ISO—OH)—HCl having 96% purity by HPLC.

Example 3

Purification of Duloxetine Hydrochloride in Ethyl Acetate 1.8 g duloxetine hydrochloride having 0.12% area by HPLC of DLX—ISO—OH was combined with 18 ml of ethyl acetate. The resulting mixture was stirred for one hour, during which time a precipitate formed. The resulting precipitate was then filtered, washed with ethyl acetate, and dried in a vacuum oven at 45° C. for 16 hours to yield duloxetine hydrochloride (97% yield) having 0.08% area by HPLC of DLX—ISO—OH.

Example 3 is repeated to obtain duloxetine hydrochloride having less than 0.02% area by HPLC of DLX—ISO—OH.

Example 4

Purification of Duloxetine Hydrochloride in Acetone 1.7 g duloxetine hydrochloride having 0.12% area by HPLC of DLX—ISO—OH was combined with 17 ml of acetone. The resulting mixture was stirred for one hour, during which time a precipitate formed. The resulting precipitate was then filtered, washed with acetone, and dried in a vacuum oven at 45° C. for 16 hours to yield duloxetine hydrochloride (91.5% yield) having less than 0.02% area by HPLC of DLX—ISO—OH.

We claim:
1. Isolated 2-(N-methyl-propanamine)-3-(2-naphthol)thiophene.
2. A process for preparing 2-(N-methyl-propanamine)-3-(2-naphthol)thiophene comprising:
   a) heating a mixture of duloxetine and at least one solvent, wherein the solvent is a $C_2$-$C_8$ ether, a $C_5$-$C_8$ aliphatic or $C_6$-$C_{12}$ aromatic hydrocarbon, a $C_1$-$C_8$ alcohol, dimethyl sulfoxide, dimethylacetamide, dimethylformamide, 1-methyl-2-pyrrolidinone, acetonitrile or propylene glycol methyl ether; and
   b) maintaining the mixture for a period of time sufficient to obtain 2-(N-methyl-propanamine)-3-(2-naphthol)thiophene.
3. The process according to claim 2, wherein the solvent is a $C_2$-$C_8$ ether, a $C_5$-$C_8$ aliphatic or $C_6$-$C_{12}$ aromatic hydrocarbon, or a $C_1$-$C_8$ alcohol.
4. The process according to claim 2, wherein the solvent is propylene glycol methyl ether or toluene.
5. The process according to claim 2, further comprising combining the mixture of step a) with at least one inorganic base.
6. The process according to claim 5, wherein the inorganic base is an alkaline metal hydroxide or an alkaline earth metal hydroxide.
7. The process according to claim 5, wherein the inorganic base is potassium hydroxide, sodium hydroxide, lithium hydroxide, magnesium hydroxide, or calcium hydroxide.
8. The process according to claim 5, wherein the inorganic base is potassium hydroxide.
9. The process according to claim 2, wherein the mixture is heated at a temperature of about 60° C. to about reflux.
10. The process according to claim 2, wherein the mixture is heated at a temperature of about reflux.
11. The process according to claim 2, wherein the mixture is maintained for at least about 96 hours.
12. The process according to claim 2, wherein the mixture is maintained for about 96 hours to about 120 hours.
13. The process according to claim 2, further comprising converting the 2-(N-methyl-propanamine)-3-(2-naphthol)thiophene to 2-(N-methyl-propanamine)-3-(2-naphthol)thiophene hydrochloride.
14. A process for preparing duloxetine hydrochloride having less than about 0.08% area by HPLC of 2-(N-methyl-propanamine)-3-(2-naphthol)thiophene comprising:
   a) providing a mixture of duloxetine hydrochloride having more than about 0.08% area by HPLC of 2-(N-methyl-propanamine)-3-(2-naphthol)thiophene in at least one polar solvent, wherein the polar solvent is a $C_{2-5}$ ketone, $C_{2-5}$ alkyl ester, $C_{2-8}$ alkyl ether or $C_{2-8}$ alkanol; and
   b) maintaining the mixture for a period of time sufficient to obtain duloxetine hydrochloride having less than about 0.08% area by HPLC of 2-(N-methyl-propanamine)-3-(2-naphthol)thiophene.
15. The process according to claim 14, wherein the polar solvent is acetone, methyl ethyl ketone, ethyl acetate, methyl t-butyl ether, ethanol, isopropanol, or n-butanol.
16. The process according to claim 14, wherein the polar solvent is acetone.
17. The process according to claim 14, wherein the mixture is maintained for at least about 1 hour.
18. The process according to claim 14, wherein the mixture is maintained for about 1 hour to about 12 hours.
19. The process according to claim 14, wherein the duloxetine hydrochloride of step b) has less than about 0.06% area by HPLC of 2-(N-methyl-propanamine)-3-(2-naphthol)thiophene.
20. The process according to claim 14, wherein the duloxetine hydrochloride of step b) has less than about 0.02% area by HPLC of 2-(N-methyl-propanamine)-3-(2-naphthol)thiophene.
21. The process according to claim 14, wherein the duloxetine hydrochloride of step b) is substantially free of 2-(N-methyl-propanamine)-3-(2-naphthol)thiophene.
22. A method of using 2-(N-methyl-propanamine)-3-(2-naphthol)thiophene as a reference marker to analyze the purity of duloxetine hydrochloride comprising:
   a) providing a reference sample comprising duloxetine hydrochloride and 2-(N-methyl-propanamine)-3-(2-naphthol)thiophene;
   b) analyzing the reference sample by HPLC and determining the relative retention time of 2-(N-methyl-propanamine)-3-(2-naphthol)thiophene compared to duloxetine hydrochloride;
   c) analyzing a sample of duloxetine hydrochloride by HPLC and determining the relative retention times of the contents of the sample as compared to duloxetine hydrochloride; and
   d) comparing the relative retention times calculated in step c) to the relative retention time calculated in step b) for 2-(N-methyl-propanamine)-3-(2-naphthol)thiophene, wherein if any of the relative retention times calculated in step c) are substantially the same as the relative retention time of 2-(N-methyl-propanamine)-3-(2-naphthol)thiophene, 2-(N-methyl-propanamine)-3-(2-naphthol)thiophene is present in the sample of duloxetine hydrochloride.
23. A method of using 2-(N-methyl-propanamine)-3-(2-naphthol)thiophene as a reference standard for determining the amount of 2-(N-methyl-propanamine)-3-(2-naphthol)thiophene in a duloxetine hydrochloride sample comprising:
   a) measuring by HPLC the area under the peak corresponding to 2-(N-methyl-propanamine)-3-(2-naphthol)thiophene in a sample of duloxetine hydrochloride having an unknown amount of 2-(N-methyl-propanamine)-3-(2-naphthol)thiophene;
   b) measuring by HPLC the area under a peak corresponding to 2-(N-methyl-propanamine)-3-(2-naphthol)thiophene in a reference standard comprising a known amount of 2-(N-methyl-propanamine)-3-(2-naphthol)thiophene; and c) determining the amount of 2-(N-methyl-propanamine)-3-(2-naphthol)thiophene in the duloxetine hydrochloride sample by comparing the area calculated in step a) to the area calculated in step b).

24. A quantification method for determining the amount of 2-(N-methyl-propanamine)-3-(2-naphthol)thiophene in a duloxetine hydrochloride sample comprising:
  a) measuring by HPLC the area under the peak corresponding to 2-(N-methyl-propanamine)-3-(2-naphthol)thiophene in a sample of duloxetine hydrochloride having an unknown amount of 2-(N-methyl-propanamine)-3-(2-naphthol)thiophene;
  b) measuring by HPLC the area under a peak corresponding to duloxetine hydrochloride in a reference standard having a known amount of duloxetine hydrochloride; and
  c) determining the amount of 2-(N-methyl-propanamine)-3-(2-naphthol)thiophene in the duloxetine hydrochloride sample by comparing the area calculated in step a) to the area calculated in step b).

25. An HPLC method for determining the amount of 2-(N-methyl-propanamine)-3-(2-naphthol)thiophene in a sample of duloxetine hydrochloride comprising:
  a) combining a sample of duloxetine hydrochloride having 2-(N-methyl-propanamine)-3-(2-naphthol)thiophene with a 1:1 (volume: volume) mixture of water and acetonitrile to form a solution, wherein the duloxetine hydrochloride is present in an amount of about 0.2 mg per milliliter of the solution;
  b) injecting the solution of step a) into a Hypersil Gold 150×4.6, 5µ column;
  c) eluting the sample from the column for about 60 min with a 63:28.8:8.2 mixture of 0.02 M $KH_2PO_4$: methanol: tetrahydrofuran and a 20:80 mixture of 0.02M $K_2HPO_4$: acetonitrile as an eluent; and
  d) measuring the 2-(N-methyl-propanamine)-3-(2-naphthol)thiophene content of the sample with a UV detector at 230 nm wavelength.

* * * * *

US007759500C1

(12) EX PARTE REEXAMINATION CERTIFICATE (9811th)
United States Patent
Ini et al.

(10) Number: US 7,759,500 C1
(45) Certificate Issued: Aug. 26, 2013

(54) 2-(N-METHYL-PROPANAMINE)-3-(2-NAPHTHOL)THIOPHENE, AN IMPURITY OF DULOXETINE HYDROCHLORIDE

(75) Inventors: Santiago Ini, Haifa (IL); Alexei Ploutno, Bat-Yam (IL); Anita Liberman, Tel-Aviv (IL); Mili Abramov, Givataim (IL); Osnat Porter-Kleks, Petach-Tikva (IL); Dina Berezovsky, Petach-Tikva (IL)

(73) Assignee: Teva Pharmaceuticals USA, Inc., North Wales, PA (US)

Reexamination Request:
No. 90/012,657, Nov. 8, 2012

Reexamination Certificate for:
Patent No.: 7,759,500
Issued: Jul. 20, 2010
Appl. No.: 11/643,693
Filed: Dec. 5, 2006

*Related U.S. Application Data*

(60) Provisional application No. 60/742,621, filed on Dec. 5, 2005.

(51) Int. Cl.
*C07D 333/12* (2006.01)
*C07D 333/20* (2006.01)

(52) U.S. Cl.
CPC .................................. *C07D 333/20* (2013.01)
USPC ............................................................ 549/74

(58) Field of Classification Search
None
See application file for complete search history.

(56) References Cited

To view the complete listing of prior art documents cited during the proceeding for Reexamination Control Number 90/012,657, please refer to the USPTO's public Patent Application Information Retrieval (PAIR) system under the Display References tab.

*Primary Examiner* — Evelyn Huang

(57) ABSTRACT

The invention encompasses 2-(N-methyl-propanamine)-3-(2-naphthol)thiophene, a duloxetine hydrochloride impurity, as well as its use as a reference marker and reference standard.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 14-21 are cancelled.

Claims 1-13 and 22-25 were not reexamined.

* * * * *